United States Patent
Pawlak, II et al.

(10) Patent No.: US 10,306,888 B2
(45) Date of Patent: Jun. 4, 2019

(54) IMAZOSULFURON MIXTURES

(71) Applicant: Valent U.S.A. LLC, Walnut Creek, CA (US)

(72) Inventors: John Andrew Pawlak, II, Lansing, MI (US); Billy Corbin, Jr., Greenville, MS (US)

(73) Assignee: VALENT U.S.A., LLC, Walnut Creek, CA (US)

( * ) Notice: Subject to any disclaimer, the term of this patent is extended or adjusted under 35 U.S.C. 154(b) by 0 days.

(21) Appl. No.: 16/110,078

(22) Filed: Aug. 23, 2018

(65) Prior Publication Data

US 2019/0059384 A1 Feb. 28, 2019

Related U.S. Application Data

(60) Provisional application No. 62/549,660, filed on Aug. 24, 2017.

(51) Int. Cl.
| | | |
|---|---|---|
| *A01N 25/30* | (2006.01) | |
| *A01N 25/34* | (2006.01) | |
| *A01N 47/36* | (2006.01) | |
| *A01N 31/08* | (2006.01) | |
| *A01N 37/00* | (2006.01) | |
| *A01N 43/08* | (2006.01) | |
| *A01N 65/18* | (2009.01) | |

(52) U.S. Cl.
CPC ............ *A01N 47/36* (2013.01); *A01N 31/08* (2013.01); *A01N 37/00* (2013.01); *A01N 43/08* (2013.01); *A01N 65/18* (2013.01)

(58) Field of Classification Search
CPC combination set(s) only.
See application file for complete search history.

(56) References Cited

U.S. PATENT DOCUMENTS

| | | | | |
|---|---|---|---|---|
| 6,936,572 | B2 * | 8/2005 | Stewart | A01N 25/04 504/362 |
| 7,651,977 | B2 * | 1/2010 | Hazen | A01N 25/30 504/141 |
| 8,138,120 | B2 * | 3/2012 | Abribat | A01N 25/04 504/116.1 |
| 8,216,976 | B2 * | 7/2012 | Hazen | A01N 25/30 504/141 |
| 8,841,235 | B2 * | 9/2014 | Kisenwether | A01N 25/30 504/127 |
| 9,456,603 | B2 * | 10/2016 | Dave | A01N 25/02 |
| 9,497,961 | B2 * | 11/2016 | Krapp | A01N 25/02 |
| 2007/0129253 | A1 * | 6/2007 | Hailu | A01N 37/22 504/358 |
| 2009/0186763 | A1 | 7/2009 | Ikeda et al. | |
| 2010/0087318 | A1 | 4/2010 | Hazen et al. | |
| 2011/0275599 | A1 * | 11/2011 | Voglewede | A01N 25/00 514/89 |
| 2017/0215418 | A1 | 8/2017 | Shinn et al. | |

FOREIGN PATENT DOCUMENTS

WO 2015/089014 A1 6/2015

OTHER PUBLICATIONS

International Search Report and Written Opinion, dated Oct. 18, 2018 in International Patent Application No. PCT/US18/47666.

\* cited by examiner

*Primary Examiner* — John Pak
(74) *Attorney, Agent, or Firm* — Wood, Phillips, Katz, Clark & Mortimer

(57) ABSTRACT

The present invention is directed to agricultural mixtures comprising imazosulfuron and a C16 to C18 fatty acid methyl ester adjuvant system. The present invention is further directed to methods of increasing the activity of imazosulfuron with the mixtures of the present invention.

19 Claims, No Drawings

IMAZOSULFURON MIXTURES

FIELD OF THE INVENTION

The present invention relates to agricultural mixtures useful for controlling undesirable plants, and methods of use thereof.

BACKGROUND OF THE INVENTION

Unwanted plants, such as weeds, reduce the amount of resources available to crop plants and can have a negative effect on crop plant yield and quality. Unwanted plants in crop plant environments include broadleaves, grasses and sedges.

Herbicides are used to control weeds in crop environments. Herbicides are expensive, and their use may result in unintentional consequences such as groundwater contamination, environmental damage, herbicide-resistant weeds, and/or human and mammalian health concerns. It is therefore desirable to minimize the amount of herbicide applied to a crop-growing environment or any area in need of weed control.

Weeds may greatly reduce yields of crop plants. For example, a weed infestation reportedly was responsible for an 80% reduction in soybean yields. Bruce, J. A., and J. J. Kells, Horseweed (*Conyza Canadensis*) control in no-tillage soybeans (*Glycine max*) with preplant and preemergence herbicides, Weed Technol. 4:642-647 (1990). Therefore, controlling weeds is a major concern of crop growers.

Further, weeds are becoming resistant to the widely-used herbicide glyphosate. As early as 2000, glyphosate-resistant horseweed was reported in Delaware. Glyphosate-resistant horseweed has since been reported in numerous states. Accordingly, there is a need for new products that can provide effective kill rates of glyphosate-resistant weeds.

Weeds are also becoming resistant to herbicides that inhibit acetolactate synthase (ALS) and protoporphyrinogen oxidase (PPO). Weeds have also been reported to be resistant to 2,4-D and dicamba. Accordingly, there is a need for new technology to control weeds that are resistant to commercially available herbicides.

In most fields throughout the Midwest and Mid-South, in-crop burndown applications are the only options for controlling weeds due to weather and timeliness of applications. Growers often find an active ingredient that is effective and the use it repeatedly. Eventually, the weeds become resistant to the active ingredient which leaves no alternatives for weed control other than mechanical removal. Mechanical removal of weeds requires extensive use of resources and is not an option for no-till or highly erodible land.

No-till farming has been increasing in popularity because it has many benefits, including decreased labor time and decreased soil erosion. However, one of the downsides of no-till farming is that weeds are harder to control in these areas because they are not subjected to tilling. Accordingly, there is an increasing need for alternative ways to handle weed infestation.

Imazosulfuron (2-chloro-N-[[(4,6-dimethoxy-2-pyrimidinyl)amino]carbonyl]imidazo[1,2-a]pyridine-3-sulfonamide) is a systemic sulfonylurea herbicide. Imazosulfuron works by inhibiting the enzyme acetolactate synthase which leads to an inhibition of amino acid synthesis. Imazosulfuron is commercially available from Valent U.S.A. LLC as League™.

Herbicides are often mixed with adjuvants to increase their effectiveness. Common adjuvants include crop oil concentrate, and "premium" adjuvant systems such as Dyne-a-Pak (available from Helena Chemical Company) which includes a proprietary blend of alkoxylated triglycerides, urea, ammonium nitrate, trisiloxane, methyl soyate, and the amine salt of alkyl ethoxylate phosphate. It is unpredictable which adjuvants out of the hundreds available would enhance the effectiveness of any herbicide against specific weeds. Further, even if an adjuvant provides increased efficacy against the weeds, it must also not increase phytotoxicity to the crop plant.

In summary, there is a need for a composition that reduces the amount of herbicide necessary to obtain sufficient weed control while minimizing the harm to crop plants. As more weeds become resistant to herbicides, alternative compositions with high weed control are desired. Further, as no-till farming continues to increase in popularity, there is a greater need for effective herbicides. A composition with effective weed control and lower dosage rate will lead to increased crop plant yields, and decreased environmental, human, and mammalian health concerns.

SUMMARY OF THE INVENTION

In one aspect, the present invention is directed to agricultural mixtures comprising imazosulfuron, or a salt thereof, and a C16 to C18 fatty acid methyl ester adjuvant system, wherein the C16 to C18 fatty acid methyl ester adjuvant system comprises from about 60 to about 99% w/w of a C16 to C18 fatty acid methyl ester mixture, from about 0.1 to about 5% w/w of a dodecylbenzene sulfonate salt, from about 0.5 to about 4% w/w of at least one dodecylbenzene sulfonate salt solvent, from about 0.1 to about 10% w/w of at least one polyoxyethylene plant oil, and from about 0.1 to about 10% w/w of at least one polyoxyethylene sorbitan ester.

In another aspect, the present invention is directed to methods for controlling weeds comprising applying the mixtures of the present invention to the area in need of weed control.

DETAILED DESCRIPTION OF THE INVENTION

It was unexpected that the mixtures of the present invention would provide superior control of some plants and increase the performance of imazosulfuron. This finding was not predictable because, as illustrated in Table 2 below, the C16 to C18 fatty acid methyl ester adjuvant system provided better efficacy than other high-cost or "premium" adjuvant systems (for example, compare treatment 6 with treatment 7). Further, the C16 to C18 fatty acid methyl ester adjuvant system provided improved efficacy when combined with some herbicides, but not all. For example, the C16 to C18 fatty acid methyl ester adjuvant system did not improve the efficacy of lactofen or flumioxazin but unexpectedly improved the efficacy of imazosulfuron (compare treatments 3 and 9 with treatment 7).

In one embodiment, the present invention is directed to agricultural mixtures comprising imazosulfuron, or a salt thereof, and a C16 to C18 fatty acid methyl ester adjuvant system, wherein the C16 to C18 fatty acid methyl ester adjuvant system comprises from about 60 to about 99% w/w of a C16 to C18 fatty acid methyl ester mixture, from about 0.1 to about 5% w/w of a dodecylbenzene sulfonate salt, from about 0.5 to about 4% w/w of at least one dodecylbenzene sulfonate salt solvent, from about 0.1 to about 10% w/w of at least one polyoxyethylene plant oil, and from about 0.1 to about 10% w/w of at least one polyoxyethylene sorbitan ester.

In a preferred embodiment, the weight to volume ratio of imazosulfuron to the C16 to C18 fatty acid methyl ester adjuvant system is from about 10:1 to about 1:1,000. In a more preferred embodiment, the weight to volume ratio of imazosulfuron to the C16 to C18 fatty acid methyl ester adjuvant system is from about 1:1 to about 1:100. In an even more preferred embodiment, the weight to volume ratio of imazosulfuron to the C16 to C18 fatty acid methyl ester adjuvant system is from about 1:5 to about 1:15. In a most preferred embodiment, the weight to volume ratio of imazosulfuron to the C16 to C18 fatty acid methyl ester adjuvant system is about 1:9.

In another embodiment, the mixtures comprise from about 0.01 to about 1% w/v imazosulfuron. In a preferred embodiment, the mixture comprises from about 0.05 to about 0.5% w/v imazosulfuron. In a more preferred embodiment, the mixture comprises from about 0.08 to about 0.2% w/v imazosulfuron and in a most preferred embodiment, the mixture comprises about 0.11% w/v imazosulfuron.

Suitable imazosulfuron salts include, but are not limited to, the ammonium salt, the lithium, sodium, potassium, magnesium, or calcium salts, organic amine salts or mixtures comprising any number of these. These examples of salts are not limiting as other salts may also be suitable for use in the present invention.

In a further embodiment, the mixtures comprise from about 0.1 to about 10% v/v of the C16 to C18 fatty acid methyl ester adjuvant system. In a preferred embodiment, the mixtures comprise from about 0.25 to about 2% v/v of the C16 to C18 fatty acid methyl ester adjuvant system. In a more preferred embodiment, the mixtures comprise from about 0.75 to about 1.5% v/v of the C16 to C18 fatty acid methyl ester adjuvant system and in a most preferred embodiment, the mixture comprises about 1% v/v of the C16 to C18 fatty acid methyl ester adjuvant system.

In an embodiment, the C16 to C18 fatty acid methyl ester adjuvant system comprises from about 80 to about 95% w/w of the C16 to C18 fatty acid methyl ester mixture. In a preferred embodiment, the C16 to C18 fatty acid methyl ester adjuvant system comprises from about 85 to about 90% w/w of the C16 to C18 fatty acid methyl ester mixture.

In an embodiment, the C16 to C18 fatty acid methyl ester adjuvant system comprises from about 0.5 to about 10% w/w of the dodecylbenzene sulfonate salt. In a preferred embodiment, the C16 to C18 fatty acid methyl ester adjuvant system comprises from about 2 to about 8% w/w of the dodecylbenzene sulfonate salt. In a more preferred embodiment, the C16 to C18 fatty acid methyl ester adjuvant system comprises from about 2 to about 6% w/w of the dodecylbenzene sulfonate salt.

In a preferred embodiment, the dodecylbenzene sulfonate salt is selected from the group consisting of calcium, sodium, potassium, or an amine salt. In a more preferred embodiment, the dodecylbenzene sulfonate salt is calcium.

In another embodiment, the concentration of the dodecylbenzene sulfonate salt in the dodecylbenzene sulfonate salt solvent is from about 50 to about 70% w/w. In a preferred embodiment, the concentration of the dodecylbenzene sulfonate salt in the dodecylbenzene sulfonate salt solvent is about 60%.

In an embodiment, the dodecylbenzene sulfonate salt solvent is an aromatic hydrocarbon. In a preferred embodiment, the dodecylbenzene sulfonate salt solvent is at least one solvent selected from the group consisting of xylene, phenylxylylethane, 2-ethyl hexanol and propylene glycol. In a more preferred embodiment, the dodecylbenzene sulfonate salt solvent is a mixture of 2-ethyl hexanol and propylene glycol.

In an embodiment, the C16 to C18 fatty acid methyl ester adjuvant system comprises from about 1 to about 5% w/w of the at least one polyoxyethylene plant oil. In a preferred embodiment, the C16 to C18 fatty acid methyl ester adjuvant system comprises from about 2 to about 4% w/w of the at least one polyoxyethylene plant oil.

In an embodiment, the at least one polyoxyethylene plant oil is selected from the group consisting of castor oil, rapeseed oil, and linseed oil. In a preferred embodiment, the polyoxyethylene plant oil is castor oil. In a more preferred embodiment, the castor oil is polyoxyethylene (54) castor oil (54 moles of ethylene oxide).

In a further embodiment, the adjuvant system comprises from about 1 to about 5% w/w of the at least one polyoxyethylene sorbitan ester. In a preferred embodiment, the adjuvant system comprises from about 1.5 to about 3.5% w/w of the at least one polyoxyethylene sorbitan ester.

In an embodiment, the polyoxyethylene sorbitan esters are ethoxylated sorbitan esters of fatty acids. In a preferred embodiment, the fatty acids are derived from animal or plant sources. Suitable polyoxyethylene sorbitan esters include sorbitan monotallate, sorbitan trioleate, sorbitan monostearate, sorbitan tristearate, sorbitan monomyristate, and sorbitan monolaurate. In a preferred embodiment, the polyoxyethylene sorbitan ester is sorbitan monotallate. In a more preferred embodiment, the polyoxyethylene sorbitan ester is POE(30) sorbitan monotallate (30 moles of ethylene oxide).

In a further embodiment, the present invention is directed to methods for increasing the activity of imazosulfuron, or a salt thereof, by applying to an area in need of weed control imazosulfuron and a C16 to C18 fatty acid methyl ester adjuvant system, wherein the C16 to C18 fatty acid methyl ester adjuvant system comprises from about 60 to about 99% w/w of a C16 to C18 fatty acid methyl ester mixture, from about 0.1 to about 5% w/w of a dodecylbenzene sulfonate salt, from about 0.5 to about 4% w/w of at least one dodecylbenzene sulfonate salt solvent, from about 0.1 to about 10% w/w of at least one polyoxyethylene plant oil, and from about 0.1 to about 10% w/w of at least one polyoxyethylene sorbitan ester.

In an embodiment, the mixture is applied at a rate of from about 50 to about 500 grams imazosulfuron per hectare. In a preferred embodiment, the mixture is applied at a rate of from about 100 to about 400 grams imazosulfuron per hectare. In a more preferred embodiment, the mixture is applied at a rate of from about 200 to about 220 grams imazosulfuron per hectare. In a most preferred embodiment, the mixture is applied at a rate of about 210 grams imazosulfuron per hectare.

In a further embodiment, the mixture is applied at a rate of from about 100 to about 20,000 milliliters of the C16 to C18 fatty acid methyl ester adjuvant system per hectare. In a preferred embodiment, the mixture is applied at a rate of from about 1,000 to about 5,000 milliliters of the C16 to C18 fatty acid methyl ester adjuvant system per hectare. In a more preferred embodiment, the mixture is applied at a rate of from about 1,500 to about 2,500 milliliters of the C16 to C18 fatty acid methyl ester adjuvant system per hectare. In a most preferred embodiment, the mixture is applied at a rate of about 1,870 milliliters of the C16 to C18 fatty acid methyl ester adjuvant system per hectare.

In another embodiment, the weed controlled is selected from the group consisting of Hemp Sesbania (*Sesbania herbacea*), Common Barnyardgrass (*Echinochloa crusgalli*), Broadleaf Signalgrass (*Brachiaria platyhylla*), and Palmer Amaranth (*Amaranthus palmeri*).

In an embodiment, the weed controlled is Hemp *Sesbania*.

In another embodiment, the weed controlled is Common Barnyardgrass.

In a further embodiment, the weed controlled is Broadleaf Signalgrass.

In yet another embodiment, the weed controlled is Palmer Amaranth.

In another embodiment, the present invention is directed to methods for controlling undesirable rice, cotton or peanut growth comprising applying imazosulfuron and a C16 to C18 fatty acid methyl ester adjuvant system to an area in need of rice, cotton or peanut growth control, wherein the C16 to C18 fatty acid methyl ester adjuvant system comprises from about 60 to about 99% w/w of a C16 to C18 fatty acid methyl ester mixture, from about 0.1 to about 5% w/w of a dodecylbenzene sulfonate salt, from about 0.5 to about 4% w/w of at least one dodecylbenzene sulfonate salt solvent, from about 0.1 to about 10% w/w of at least one polyoxyethylene plant oil, and from about 0.1 to about 10% w/w of at least one polyoxyethylene sorbitan ester.

In a further embodiment, the area in need of weed control is an area occupied by rice, soybean, cotton, peanut or corn plants.

The mixtures of the present invention can be applied post emergence and as a burndown treatment.

The herbicide mixtures of the present invention can be applied by any convenient means. Those skilled in the art are familiar with the modes of application that include foliar applications such as spraying, chemigation (a process of applying the mixture through the irrigation system), by granular application, or by impregnating the mixture on fertilizer.

The herbicide mixtures of the present invention can be prepared as concentrate formulations or as ready-to-use formulations. The mixtures can be tank mixed.

The herbicide mixtures of the present invention can be formulated to contain additional adjuvants, such as solvents, anti-caking agents, stabilizers, defoamers, slip agents, humectants, dispersants, wetting agents, thickening agents, emulsifiers, and preservatives which increase the long-lasting activity of the actives. Other components that enhance the biological activity of these ingredients may optionally be included.

The herbicide mixtures of the present invention can also include one or more additional herbicides.

The mixtures of the present invention can be applied to any environment in need of weed or undesirable plant growth control. The environment in need of weed or undesirable plant growth control may include any area that is desired to have a reduced number of weeds or to be free of weeds. For example, the mixture can be applied to an area used to grow crop plants, such as a field, orchard, or vineyard. Applicant's mixtures and methods can be applied to areas where rice, soybean, cotton, peanut and corn plants are growing. The compositions of the present invention can also be applied to non-agricultural areas in need of weed control such as a lawns, golf courses, or parks.

Applicant's mixtures and methods can be applied successfully to crop plants and weeds that are resistant to glyphosate, glufosinate, or other herbicides. The composition and methods can also be applied to areas where genetically modified crops ("GMOs") or non-GMO crops are growing. The term "GMO crops" as used herein refers to crops that are genetically modified.

Throughout the application, the singular forms "a," "an," and "the" include plural reference unless the context clearly dictates otherwise.

As used herein, "C16 to C18 fatty acid methyl esters adjuvant system" or "adjuvant system" refers to an adjuvant formulation comprising a C16 to C18 fatty acid methyl ester mixture, a dodecylbenzene sulfonate salt, at least one dodecylbenzene sulfonate salt solvent, at least one polyoxyethylene plant oil, and at least one polyoxyethylene sorbitan ester.

As used herein, "dodecylbenzene sulfonate salt solvent" refers to a solvent that will dissolve a salt of dodecylbenzene sulfonate.

As used herein, "g ai/ha" is an abbreviation for grams of active ingredient per hectare.

As used herein, "% v/v" refers to the volume of the adjuvant used compared to the total volume of the mixture or adjuvant system.

As used herein, "% w/w" refers to the weight of the component compared to the total weight of the mixture or adjuvant system.

As used herein, all numerical values relating to amounts, weight percentages and the like are defined as "about" or "approximately" each particular value, plus or minus 10%. For example, the phrase "at least 5.0% by weight" is to be understood as "at least 4.5% to 5.5% by weight." Therefore, amounts within 10% of the claimed values are encompassed by the scope of the claims.

As used herein, "post emergence" refers to an herbicide treatment that is applied to an area after the weeds have germinated and emerged from the ground or growing medium.

As used herein, "burndown" refers to when an herbicide is used to reduce weed presence at the time of treatment. Burndown is often used in minimum or no-till fields because the weeds cannot be managed by tilling the soil. The burndown application may be used post-harvest and/or prior to crop emergence. Burndown is especially useful against weeds that emerge between growing seasons.

Applicant has referred to developmental stages in the following examples as "V" stages. The "V" stages are designated numerically as V1, V2, V3, etc. In this identification system of V(n), (n) represents the number of leaves with visible collars. Each leaf stage is defined according to the uppermost leaf whose leaf collar is visible.

These representative embodiments are in no way limiting and are described solely to illustrate some aspects of the invention.

Further, the following examples are offered by way of illustration only and not by way of limitation.

EXAMPLES

Example 1

An adjuvant system was prepared using the amounts of the components listed in Table 1 below. The components may be added in any order and should be mixed until homogeneous.

The C16 to C18 fatty acid methyl esters mixture (CAS 67762-38-3) used was CE-1618 (comprising 23 to 32% C16, 65 to 75% C18) and is available from Proctor and Gamble.

Witconate P-1220EH (available from AkzoNobel N.V.) was used as the source of the 60% calcium dodecylbenzene sulfonate in (25%) 2-ethyl hexanol and (15%) propylene glycol (CAS 26264-06-2).

Emulpon™ CO-550 (available from AkzoNobel N.V.) was used as the source of the POE(54) castor oil (CAS 61791-12-6).

Armotan® AL-69-66 (available from and a registered trademark of AkzoNobel N.V.) was used as the source of the sorbitan monotallate (CAS 68953-01-5).

TABLE 1

| Component | % w/w |
|---|---|
| C16 to C18 fatty acid methyl esters mixture | 88.3 |
| 60% Dodecylbenzene sulfonate salt in 2-ethyl hexanol and propylene glycol | 6.2 (3.72 DDBs) |
| POE(54) castor oil | 2.9 |
| POE(30) sorbitan monotallate | 2.6 |
| Total | 100 |

Example 2

A field trial was conducted in Mississippi, United States, to evaluate the impact of the C16 to C18 fatty acid methyl esters adjuvant system on the effectiveness of several herbicides. Rice, soybeans, cotton, peanut and corn seeds were planted and irrigated on two days after planting. Seven days after planting there was good stand of all the crops, except only 4 of the 9 rows of rice were visible. The weeds were about 3 centimeters tall at this time. The treatments in Table 2 below were applied 13 days after planting. The rate of each treatment is below in Table 2 and all the adjuvant systems were mixed with the herbicides at a rate of 1% v/v.

At the time of treatment: Hemp *Sesbania* was at the V4 growth stage and from about 3 to 5 about inches tall; Ivyleaf Morningglory was at the V3 growth stage and from about 2 to about 4 inches tall; Common Barnyardgrass was at the V5 growth stage and from about 2.5 to about 6 inches tall; Palmer Amaranth was at the vegetative growth stage and from about 2 to about 7 inches tall; Yellow Nutsedge was at the V8 growth stage and from about 3 to about 6 inches tall; and Broadleaf Signalgrass was at the second true leaf growth stage and from about 2 to about 4 inches tall.

At the time of treatment: rice was at the first true leaf growth stage and from about 5 to 7 inches tall; soybeans were at the V2 growth stage and from about 5 to 7 inches tall; cotton was at the V2 growth stage and from about 5 to 7 inches tall; peanut was at the V5 growth stage and from about 3 to 5 inches tall; and corn was at the V3 growth stage and from about 9 to 12 inches tall.

The weeds were evaluated fourteen days after treatment.

The adjuvant system described in Example 1 above was used as the source of the C16 to C18 fatty acid methyl esters adjuvant system used in this study.

League™ herbicide was used as the source of imazosulfuron. League™ is a 75% imazosulfuron water dispersible granule formulation available from Valent U.S.A. LLC.

Regiment® was used as the source of bispyribac-sodium. Regiment® is an 80% bispyribac-sodium formulation available from (and a registered trademark of) Valent U.S.A. LLC.

Cobra® herbicide was used as the source of lactofen. Cobra® is a 24% lactofen formulation available from (and a registered trademark of) Valent U.S.A. LLC.

Valor® herbicide was used as the source of flumioxazin. Valor® is a 51% flumioxazin water dispersible granule formulation available from (and a registered trademark of) Valent U.S.A. LLC.

Agridex® (available from and a registered trademark of Bayer CropSciences) was the source of the adjuvant comprising a proprietary blend of heavy range, paraffin-based petroleum oil and nonionic emulsifiers.

Dyne-a-Pak, available from Helena Chemical Company, was used as the source of the adjuvant comprising a proprietary blend of alkoxylated triglyceride, urea, ammonium nitrate, trisiloxane, methyl soyate, and the amine salt of alkyl ethoxylate phosphate (CAS 5905-50106-AA).

TABLE 2

| Treatment | Herbicide and Adjuvant | Rate (grams of ai per hectare) | *Sesbania*, Hemp | Morningglory Ivyleaf | Barnyardgrass, Common | Signalgrass, Broadleaf | Amaranth, Palmer | Nutsedge, Yellow |
|---|---|---|---|---|---|---|---|---|
| 1 | Untreated Control | — | 0 g | 0 e | 0 f | 0 e | 0 g | 0 g |
| 2 | Flumioxazin Blend of heavy range, paraffin-based petroleum oil and nonionic emulsifiers | 71.5 | 100 a | 80 bc | 35 d | 20 d | 99.3 a | 55 cd |
| 3 | Flumioxazin C16 to C18 Fatty Acid Methyl Esters Adjuvant System | 71.5 | 96.7 ab | 69.3 c | 20 e | 18.3 d | 100 a | 26.7 efg |
| 4 | Bispyribac-sodium Blend of alkoxylated triglyceride, urea, ammonium nitrate, trisiloxane, methyl soyate, and the amine salt of alkyl ethoxylate phosphate | 28 | 90.3 abc | 33.3 d | 93.3 ab | 81.7 a | 69.3 d | 61.7 bc |
| 5 | Bispyribac-sodium C16 to C18 Fatty Acid Methyl Esters Adjuvant System | 28 | 91.7 ab | 41.7 d | 100 a | 85 a | 76 c | 50 cde |
| 6 | Imazosulfuron blend of alkoxylated | 210 | 79.3 cd | 85 abc | 15 ef | 18.3 d | 51.7 f | 90 a |

TABLE 2-continued

| Treatment | Herbicide and Adjuvant | Rate (grams of ai per hectare) | *Sesbania*, Hemp | Morningglory Ivyleaf | Barnyardgrass, Common | Signalgrass, Broadleaf | Amaranth, Palmer | Nutsedge, Yellow |
|---|---|---|---|---|---|---|---|---|
| | triglyceride, urea, ammonium nitrate, trisiloxane, methyl soyate, and the amine salt of alkyl ethoxylate phosphate | | | | | | | |
| 7 | Imazosulfuron C16 to C18 Fatty Acid Methyl Esters Adjuvant System | 210 | 94 ab | 90 ab | 53.3 c | 35 c | 61.7 e | 87.7 ab |
| 8 | Lactofen Blend of heavy range, paraffin-based petroleum oil and nonionic emulsifiers | 140 | 86.7 bcd | 6.7 e | 6.7 ef | 0 e | 85 b | 31.7 def |
| 9 | Lactofen C16 to C18 Fatty Acid Methyl Esters Adjuvant System | 140 | 78.3 d | 3.3 e | 3.3 f | 0 e | 89.3 b | 18.3 fg |

Means followed by the same letter in each column do not significantly differ.

This study shows that the C16 to C18 fatty acid methyl esters adjuvant system increases the effectiveness of imazosulfuron on Hemp *Sesbania*, Common Barnyardgrass, Broadleaf Signalgrass, and Palmer Amaranth. This was unexpected because it did not increase the effectiveness of imazosulfuron on Ivyleaf Morningglory and Yellow Nutsedge. Further, this was unexpected because the C16 to C18 fatty acid methyl esters adjuvant system failed to increase the effectiveness of lactofen and flumioxazin.

In this study, phytotoxicity of the crops was also evaluated. Table 3 shows the results of these observations on rice, soybeans, cotton, peanut and corn.

Means followed by the same letter in each column do not significantly differ.

As seen in Table 3 above, the C16 to C18 fatty acid methyl esters adjuvant system of the present invention did not significantly increase phytotoxicity of imazosulfuron on rice, soybean, cotton, peanut or corn. Accordingly, the mixtures of the present invention are an effective treatment for removing weeds among common crop plants without increasing phytotoxicity to the crop plant.

What is claimed is:

1. An agricultural mixture comprising imazosulfuron, or a salt thereof, and a C16 to C18 fatty acid methyl ester adjuvant system, wherein the C16 to C18 fatty acid methyl ester adjuvant system comprises from about 60 to about 99%

TABLE 3

| Treatment | Herbicide and Adjuvant | Rice | Soybean | Cotton | Peanut | Corn |
|---|---|---|---|---|---|---|
| 1 | Untreated Control | 0 e | 0 d | 0 d | 0 g | 0 e |
| 2 | Flumioxazin Blend of heavy range, paraffin-based petroleum oil and nonionic emulsifiers | 21.7 d | 45 b | 100 a | 61.7 d | 31.7 c |
| 3 | Flumioxazin C16 to C18 Fatty Acid Methyl Esters Adjuvant System | 43.3 c | 46.7 b | 100 a | 56.7 d | 31.7 c |
| 4 | Bispyribac-sodium Blend of alkoxylated triglyceride, urea, ammonium nitrate, trisiloxane, methyl soyate, and the amine salt of alkyl ethoxylate phosphate | 0 e | 98.7 a | 98.7 a | 36.7 e | 81.7 b |
| 5 | Bispyribac-sodium C16 to C18 Fatty Acid Methyl Esters Adjuvant System | 0 e | 98.3 a | 93.3 a | 36.7 e | 88.3 ab |
| 6 | Imazosulfuron blend of alkoxylated triglyceride, urea, ammonium nitrate, trisiloxane, methyl soyate, and the amine salt of alkyl ethoxylate phosphate | 0 e | 0 d | 60 c | 55 d | 20 d |
| 7 | Imazosulfuron C16 to C18 Fatty Acid Methyl Esters Adjuvant System | 0 e | 0 d | 66.7 bc | 60 d | 20 d |
| 8 | Lactofen Blend of heavy range, paraffin-based petroleum oil and nonionic emulsifiers | 23.3 d | 16.7 c | 71.7 b | 8.3 fg | 15 d |
| 9 | Lactofen C16 to C18 Fatty Acid Methyl Esters Adjuvant System | 23.3 d | 11.7 c | 65 bc | 11.7 f | 15 d | w/w of a C16 to C18 fatty acid methyl ester mixture, from about 0.1 to about 5% w/w of a dodecylbenzene sulfonate salt, from about 0.5 to about 4% w/w of at least one dodecylbenzene sulfonate salt solvent, from about 0.1 to about 10% w/w of at least one polyoxyethylene plant oil, and from about 0.1 to about 10% w/w of at least one polyoxyethylene sorbitan ester.

2. The mixture of claim 1 wherein the weight to volume ratio of imazosulfuron to the C16 to C18 fatty acid methyl esters adjuvant system is from about 1:1 to about 1:100.

3. The mixture of claim 1 wherein the mixture comprises from about 0.01 to about 1.0% w/v imazosulfuron.

4. The mixture of claim 1 wherein the mixture comprises from about 0.1 to about 10% v/v of the C16 to C18 fatty acid methyl ester adjuvant system.

5. The mixture of claim 1 wherein the C16 to C18 fatty acid methyl esters adjuvant system comprises from about 0.5 to about 10% w/w of the dodecylbenzene sulfonate salt.

6. The mixture of claim 1 wherein the dodecylbenzene sulfonate salt is calcium.

7. The mixture of claim 1 wherein the C16 to C18 fatty acid methyl ester adjuvant system comprises from about 1 to about 5% w/w of the at least one polyoxyethylene plant oil.

8. The mixture of claim 1 wherein the polyoxyethylene plant oil is castor oil.

9. The mixture of claim 1 wherein the adjuvant system comprises from about 1 to about 5% w/w of the at least one polyoxyethylene sorbitan ester.

10. The mixture of claim 1 wherein the polyoxyethylene sorbitan ester is sorbitan monotallate.

11. A method of increasing the activity of imazosulfuron, or a salt thereof, by applying to an area in need of weed control imazosulfuron and a C16 to C18 fatty acid methyl ester adjuvant system, wherein the C16 to C18 fatty acid methyl ester adjuvant system comprises from about 60 to about 99% w/w of C16 to C18 fatty acid methyl ester mixture, from about 0.1 to about 5% w/w of a dodecylbenzene sulfonate salt, from about 0.5 to about 4% w/w of a dodecylbenzene sulfonate salt solvent, from about 0.1 to about 10% w/w of at least one polyoxyethylene plant oil, and from about 0.1 to about 10% w/w of at least one polyoxyethylene sorbitan ester.

12. The method of claim 11 wherein the imazosulfuron is applied at a rate of from about 50 to about 500 grams per hectare.

13. The method of claim 11 wherein the C16 to C18 fatty acid methyl ester adjuvant system is applied at a rate of from about 1,000 to about 5,000 milliliters per hectare.

14. The method of claim 11 wherein the weed controlled is selected from the group consisting of Hemp *Sesbania* (*Sesbania herbacea*), Common Barnyardgrass (*Echinochloa crus-galli*), Broadleaf Signalgrass (*Brachiaria platyhylla*), and Palmer Amaranth (*Amaranthus palmeri*).

15. The method of claim 14 wherein the weed controlled is Hemp *Sesbania*.

16. The method of claim 14 wherein the weed controlled is Common Barnyardgrass.

17. The method of claim 14 wherein the weed controlled is Broadleaf Signalgrass.

18. The method of claim 14 wherein the weed controlled is Palmer Amaranth.

19. The method of claim 11 wherein the area in need of weed control is occupied by rice, soybean, cotton, peanut or corn plants.

\* \* \* \* \*